(12) United States Patent
Proniuk (10) Patent No.: US 9,193,757 B2
(45) Date of Patent: Nov. 24, 2015

(54) ONAPRISTONE POLYMORPHIC FORMS AND METHODS OF USE

(71) Applicant: ARNO THERAPEUTICS, Flemington, NJ (US)

(72) Inventor: Stefan Proniuk, Weehawken, NJ (US)

(73) Assignee: ARNO THERAPEUTICS, INC., Flemington, NJ (US)

( * ) Notice: Subject to any disclaimer, the term of this patent is extended or adjusted under 35 U.S.C. 154(b) by 0 days.

(21) Appl. No.: 14/203,814

(22) Filed: Mar. 11, 2014

(65) Prior Publication Data

US 2014/0271819 A1 Sep. 18, 2014

Related U.S. Application Data

(60) Provisional application No. 61/777,752, filed on Mar. 12, 2013.

(51) Int. Cl.
| | |
|---|---|
| *A61K 9/127* | (2006.01) |
| *A61K 38/00* | (2006.01) |
| *A61P 35/00* | (2006.01) |
| *C07J 41/00* | (2006.01) |
| *A61K 31/575* | (2006.01) |
| *A61K 45/06* | (2006.01) |
| *A61K 31/565* | (2006.01) |
| *A61K 31/569* | (2006.01) |

(52) U.S. Cl.
CPC ............ *C07J 41/0083* (2013.01); *A61K 31/565* (2013.01); *A61K 31/569* (2013.01); *A61K 31/575* (2013.01); *A61K 45/06* (2013.01); *C07J 41/00* (2013.01)

(58) Field of Classification Search
None
See application file for complete search history.

(56) References Cited

U.S. PATENT DOCUMENTS

| | | | |
|---|---|---|---|
| 4,780,461 | A | 10/1988 | Neef et al. |
| 5,273,971 | A | 12/1993 | Scholz et al. |
| 5,446,036 | A | 8/1995 | Scholz et al. |

FOREIGN PATENT DOCUMENTS

DE 3321826 12/1984

OTHER PUBLICATIONS

International Application No. PCT/US2014/023651, Written Opinion dated Jul. 28, 2014, 11 pgs.
Robertson et al., Onapristone, a Progesterone Receptor Antagonist, as First-line Therapy in Primary Breast Cancer; 1999; European J. of Cancer; 35(2) 214-218.
Klijn et al., Progesterone antagonists and progesterone receptor modulation in the treatment of breast cancer; Steroids; 2000; 825-830; Elsevier Science Inc.
Jonat et al., The clinican efficacy of progesterone antagonists in breast cancer; Endocrine Therapy of Breast Cancer; 117-124.
Neef et al., New Steroids with Antiprogestational and Antiglucocorticoid Activities; Steroids; 1984; vol. 44, No. 4; 349-372.
Brittain et al., Polymorphism in Pharmaceutical Solids; 2009; 2nd edition; Informa Healthcare Press, New York.
Bernstein et al., Polymorphism in Molecular Crystals; 2002; Clarendon Press, Oxford.
Hilfiker et al., Polymorphism in the Pharmaceutical Industry; 2006; Wiley-VCH, Weinheim.

*Primary Examiner* — Craig Ricci
*Assistant Examiner* — Jared D Barsky
(74) *Attorney, Agent, or Firm* — VLP Law Group LLP; Jeremy A. Cubert (57) ABSTRACT

Polymorphic forms of onapristone and methods of making and using such polymorphic forms are provided. Crystalline polymorphic forms can be characterized by their X-ray powder diffraction patterns and other properties.

8 Claims, 14 Drawing Sheets

FIG. 1

DSC Form A

FIG. 2

HR-XRPD Form A

TGA AND SDTA Form B

FIG. 5

DSC Form B

TGA and SDTA Form C

XRPD Form C

ONAPRISTONE POLYMORPHIC FORMS AND METHODS OF USE

PRIORITY CLAIM

This application claims priority to U.S. Provisional Patent Application Ser. No. 61/777,752, filed Mar. 12, 2013. The above referenced application is incorporated herein by reference as if restated in full.

BACKGROUND

Onapristone (ONA) is an anti-progestin drug and progesterone receptor antagonist which was originally developed for contraceptive use. However, it has demonstrated substantial activity in advanced breast cancer. While onapristone has previously been investigated as a potential therapeutic agent for breast cancer, its development was stopped due to toxicity concerns. Robertson et al., Onapristone, a Progesterone Receptor Antagonist, as First-line Therapy in Primary Breast Cancer European J. of Cancer 35(2) 214-218 (1999). It is thought that ONA binds to the progesterone receptor (PR), preventing the PR from binding to DNA and thereby inhibiting or eliminating PR-induced transcription. See, e.g., Klijn et al., Progesterone antagonists and progesterone receptor modulation in the treatment of breast cancer, Steroids, v. 65, pp. 825-830 (2000); Jonatt et al., The clinical efficacy of progesterone antagonists in breast cancer, Endocrine Therapy of Breast Cancer, pp. 117-124.

Onapristone is known to be an amorphous compound. For example, (3-Acyloxypropyl)-derivatives of Onapristone are crystalline in comparison to the parent compound. Neef, G.; Wiechert, R.; Beier, S.; Elger, W.; Henderson, D. UP 4,780461, 1988. Onapristone has previously been isolated as an amporphous solid and as a yellow oil. Neef, G.; Wiechert, R.; Beier, S.; Elger, W.; Henderson, D. Steroids, 1984, 44, 349; Neef, G Sauer, G.; Wiechert, R.; Beier, S.; Elger, W.; Henderson, D.; Rohde, R. DE3321826, 1984.

The term "polymorph" or "polymorphic" refers to different crystalline forms of a chemical compound. Polymorphic or crystalline forms of a compound may possess properties that affect the solubility, stability, bioavailability, and efficacy of a compound. Polymorphic forms of a compound can be compared, for example, to amorphous forms or other crystalline forms with respect to thermodynamic behaviors measured by a variety of techniques including, but not limited to, melting point, thermogravimetric analysis (TGA), differential scanning calorimetry (DSC), x-ray powder diffraction (XRPD), high performance liquid chromatography (HPLC), Raman microscopy, FT-IR spectroscopy, mass spectrometry (MS), and thermogravimetric analysis coupled with mass spectrometry (TG-MS). The physical stability of crystalline forms can be measured, for example, under conditions where the temperature and humidity in the environment are controlled for various time periods.

SUMMARY

Aspects disclosed herein provide polymorphic or crystalline forms of ONA, also known Onapristone, (e.g., (8S,11R, 13R, 14S,17S)-11-[4-(dimethylamino)phenyl]-17-hydroxy-17-(3-hydroxypropyl)-13-methyl-1,2,6,7,8,11,12,14,15,16-decahydrocyclopenta[a]phenanthren-3-one) having the following chemical structure:

In one aspect, these polymorph or crystalline forms of ONA are advantageously crystalline in comparison to previously isolated amorphous forms. Crystalline forms of compounds, for example, are typically more stable, have lower solubility, and may have higher bioavailability.

In one aspect, the polymorphic forms include salts, solvates, hydrates, anhydrous, co-crystalline and other crystalline forms and combinations. The polymorphic forms can be formulated into a variety of dosage forms having increased stability, increased bioavailability, sustained release, and other properties. Polymorphic forms of ONA described herein are characterized by methods including high resolution X-ray powder diffraction patterns (HR-XRPD), X-ray powder diffraction patterns (XRPD), differential scanning calorimetry (DSC), and thermogravimetry mass spectrometry (TG-MS).

In another aspect, polymorphic forms of ONA can be made by combining ONA with any of the following exemplary solvents: water, methanol, ethanol, isopropanol, acetone, butanone, 2-, ethyl acetate, dioxane, 1,4-, tert-Butyl methyl ether, tetrahydrofuran, acetonitrile, chloroform, cyclohexane, n-heptane, toluene, xylene, p-, cumene, anisole, ethyl formate, and butyl acetate.

In one aspect, the ONA polymorphic forms can be made by mixing ONA or a salt thereof with any of the above solvents, or other suitable solvents, with or without heating of the mixture and subsequent cooling and or evaporation of the solvents at various rates in order to form precipitated material which can be analyzed as described herein.

DETAILED DESCRIPTION

Before describing several exemplary aspects described herein, it is to be understood that the invention is not limited to the details of construction or process steps set forth in the following description. The aspects described herein are capable of being practiced or being carried out in various ways.

Aspects described herein provide polymorphic forms of ONA which have advantageous properties including but not limited to increased bioavailability, increased stability, and increased solubility. In one aspect, these properties relate to properties that will impart advantages with respect to formulating ONA into a suitable dosage form.

Polymorphic forms of ONA have varying physical and chemical properties with respect, for example, solubility, melting temperature, hygroscopy, and vapor pressure which may affect the stability of a particular dosage form of ONA. Drug formulation and dosage form selection have a significant impact on the cost of manufacturing. Stability of a particular dosage form may also significantly impact the shelf life of the drug, required frequency of refills, and the cost of the drug to the patient. Thus, selecting a polymorphic form with desired chemical properties may affect the cost and ease of manufacture, the effectiveness of the drug, and the cost and convenience of using the drug for the patient.

Physical properties such as flow, particle size, surface area, and hardness may significantly impact the pharmacokinetics of the drug. For example, the dissolution and subsequent absorption of the drug in the body will affect the maximum concentration in the blood, clearance of the drug, and whether the drug is resident in the body for the optimal period of time.

Polymorphic forms of ONA were identified by conducting solubility assessments in a variety of solvents (e.g., water, methanol, ethanol, isopropanol, acetone, butanone, 2-, ethyl acetate, dioxane, 1,4-, tert-Butyl methyl ether, tetrahydrofuran, acetonitrile, chloroform, cyclohexane, n-heptane, toluene, xylene, p-, cumene, anisole, ethyl formate, and butyl acetate). The resulting polymorphic forms of ONA were characterized by methods including HR-XRPD (high resolution), XRPD, TGA and SDTA, and DSC.

TABLE 2

Experimental conditions for the 40 slurry conversions and evaporative crystallization

| xp ID | Mass Onapristone (mg) | Volume (µl) | Solvent | Slurry at T° C. | Temperature (° C.) |
|---|---|---|---|---|---|
| SA1 | 26.9 | 400 | Water | Yes | 25 |
| SA2 | 27.7 | 400 | Methanol | Yes | 25 |
| SA3 | 28.3 | 200 | Ethanol | Yes | 25 |
| SA4 | 24.9 | 200 | Isopropanol | Yes | 25 |
| SA5 | 21.2 | 200 | Acetone | Yes | 25 |
| SA6 | 25.3 | 200 | Butanone, 2- | Yes | 25 |
| SA7 | 25.6 | 200 | Ethyl acetate | Yes | 25 |
| SA8 | 40.1* | 200 | Dioxane, 1,4- | No | 25 |
| SA9 | 24.4 | 200 | Tert-Butyl methyl ether | Yes | 25 |
| SA10 | 53.6 | 200 | Tetrahydrofuran | No | 25 |
| SA11 | 27.1 | 200 | Acetonitrile | Yes | 25 |
| SA12 | 39.0* | 200 | Chloroform | No | 25 |
| SA13 | 21.6 | 400 | Cyclohexane | Yes | 14 |
| SA14 | 22.7 | 400 | n-Heptane | Yes | 25 |
| SA15 | 22.7 | 400 | Toluene | Yes | 25 |
| SA16 | 20.2 | 400 | Xylene, p- | Yes | 25 |
| SA17 | 25.8 | 400 | Cumene | Yes | 25 |
| SA18 | 20.7 | 200 | Anisole | Yes | 25 |
| SA19 | 20.4 | 200 | Ethyl formate | Yes | 25 |
| SA20 | 21.2 | 200 | Butyl acetate | Yes | 25 |
| SA21 | 28.7 | 400 | Water | Yes | 25 |
| SA22 | 62.5* | 400 | Methanol | Yes | 25 |
| SA23 | 57.1* | 200 | Ethanol | No | 25 |
| SA24 | 60.4* | 200 | Isopropanol | Yes | 50 |
| SA25 | 58.0* | 200 | Acetone | Yes | 50 |
| SA26 | 62.2* | 200 | Butanone, 2- | Yes | 50 |
| SA27 | 29.2 | 200 | Ethyl acetate | Yes | 50 |
| SA28 | 53.5* | 200 | Dioxane, 1,4- | No | 50 |
| SA29 | 31.7 | 200 | Tert-Butyl methyl ether | Yes | 50 |
| SA30 | 61.4* | 200 | Tetrahydrofuran | No | 50 |
| SA31 | 29.9 | 200 | Acetonitrile | Yes | 50 |
| SA32 | 61.4* | 200 | Chloroform | No | 50 |
| SA33 | 34.6 | 400 | Cyclohexane | Yes | 50 |
| SA34 | 32.3 | 400 | n-Heptane | Yes | 50 |
| SA35 | 33.5 | 400 | Toluene | Yes | 50 |
| SA36 | 30.5 | 400 | Xylene, p- | Yes | 50 |
| SA37 | 32.7 | 400 | Cumene | Yes | 50 |
| SA38 | 57.0* | 200 | Anisole | Yes | 50 |
| SA39 | 29.4 | 200 | Ethyl formate | Yes | 50 |
| SA40 | 32.8 | 200 | Butyl acetate | Yes | 50 |

*Extra material was added since the initial dissolved.

Methods for obtaining and characterizing polymorphic forms generally are known in the art as shown, for example, in H. G. Brittain, "Polymorphism in Pharmaceutical Solids", 2nd edition [Informa Healthcare Press, New York, 2009], J. Bernstein, "Polymorphism in Molecular Crystals" [Clarendon Press, Oxford, 2002], and R. Hilfiker, "Polymorphism in the Pharmaceutical Industry [Wiley-VCH, Weinheim, 2006], incorporated by reference herein in their entirety.

Figure 1:
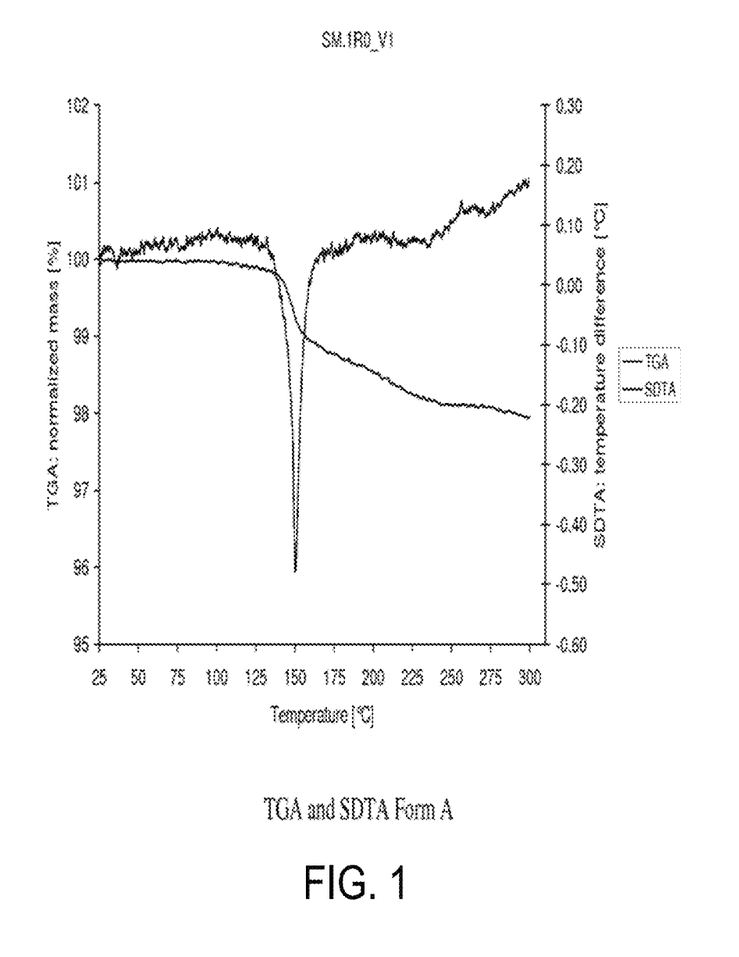
FIG. 1 shows an exemplary TGA and SDTA spectra corresponding to ONA polymorphic form A.
Figure 2:
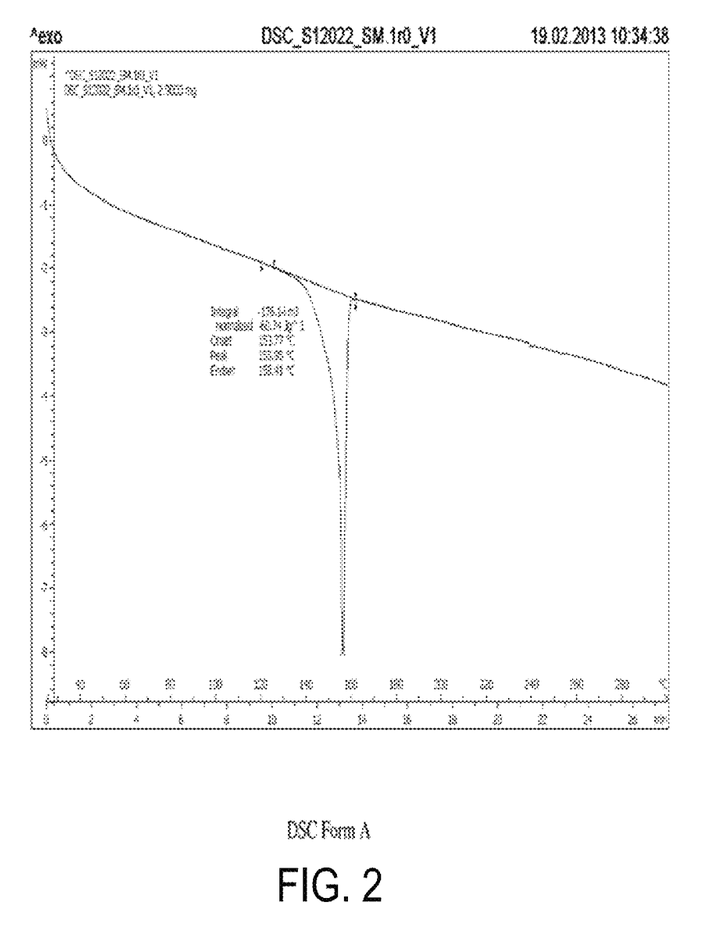
FIG. 2 shows an exemplary DSC corresponding to ONA polymorphic form A.
Figure 3:
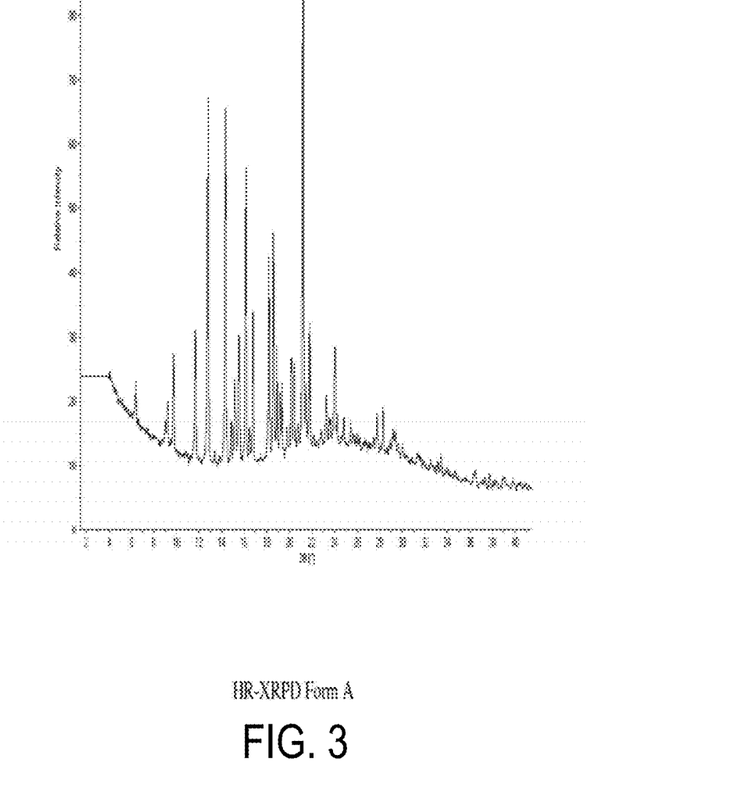
FIG. 3 shows an exemplary HR-XRPD pattern corresponding to ONA polymorphic form A.

In one aspect, ONA polymorphic form A has the HR-XRPD pattern as shown in FIG. 3.

Figure 4:
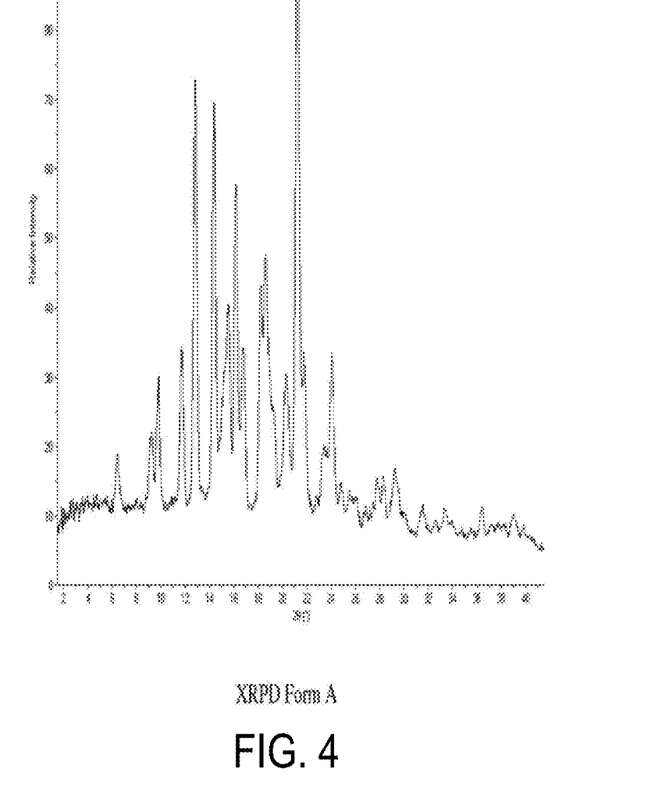
FIG. 4 shows an exemplary XRPD pattern corresponding to ONA polymorphic form A.
Figure 5:
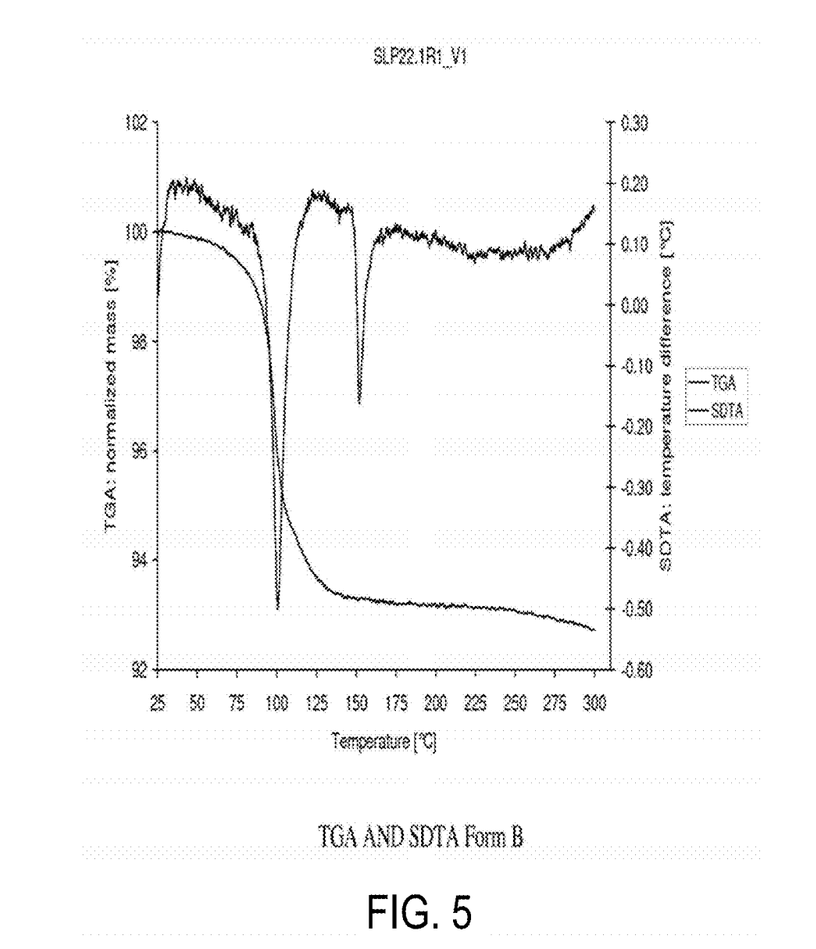
FIG. 5 shows an exemplary TGA and SDTA spectra corresponding to ONA polymorphic form B.
Figure 6:
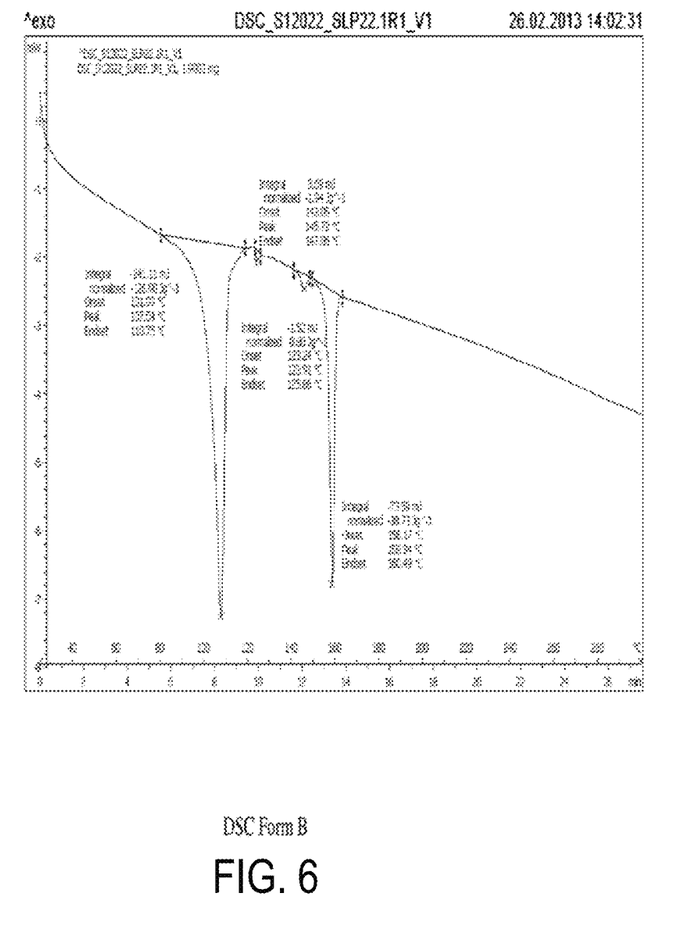
FIG. 6 shows an exemplary DSC corresponding to ONA polymorphic form B.

In one aspect, ONA polymorphic form A has the XRPD pattern as shown in FIG. 4.

Figure 7:
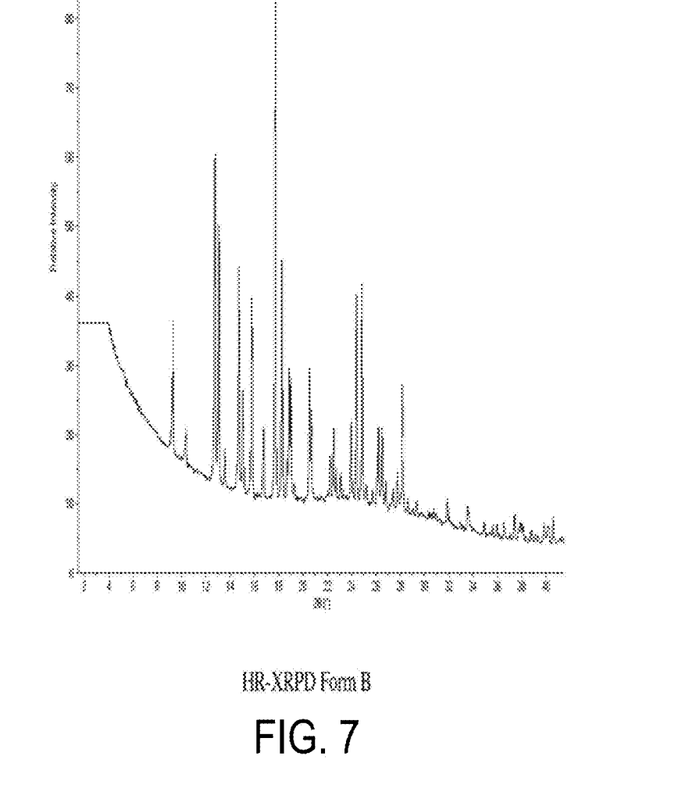
FIG. 7 shows an exemplary HR-XRPD pattern corresponding to ONA polymorphic form B.

In one aspect, ONA polymorphic form B has the HR-XRPD pattern as shown in FIG. 7.

Figure 8:
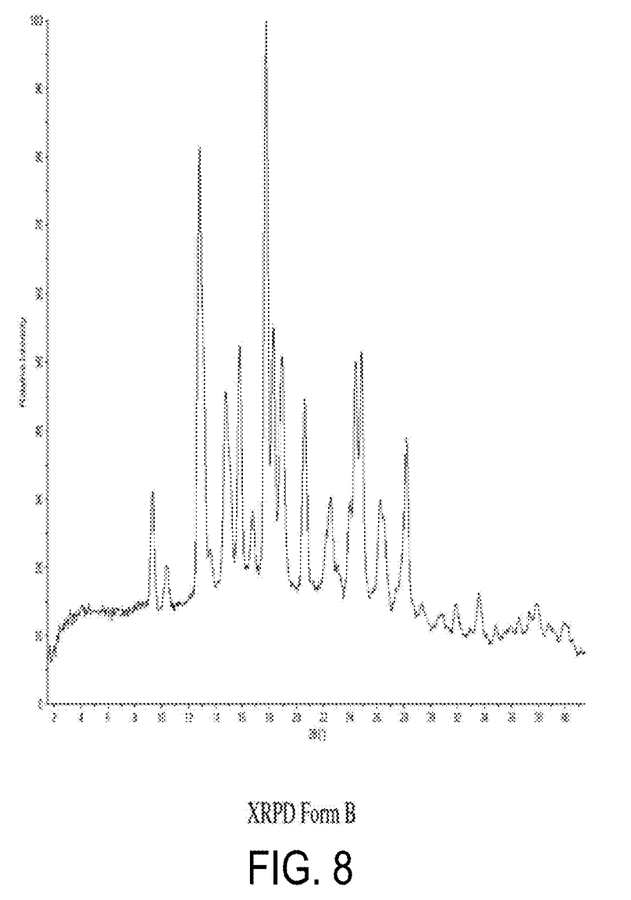
FIG. 8 shows an exemplary XRPD pattern corresponding to ONA polymorphic form B.
Figure 9:
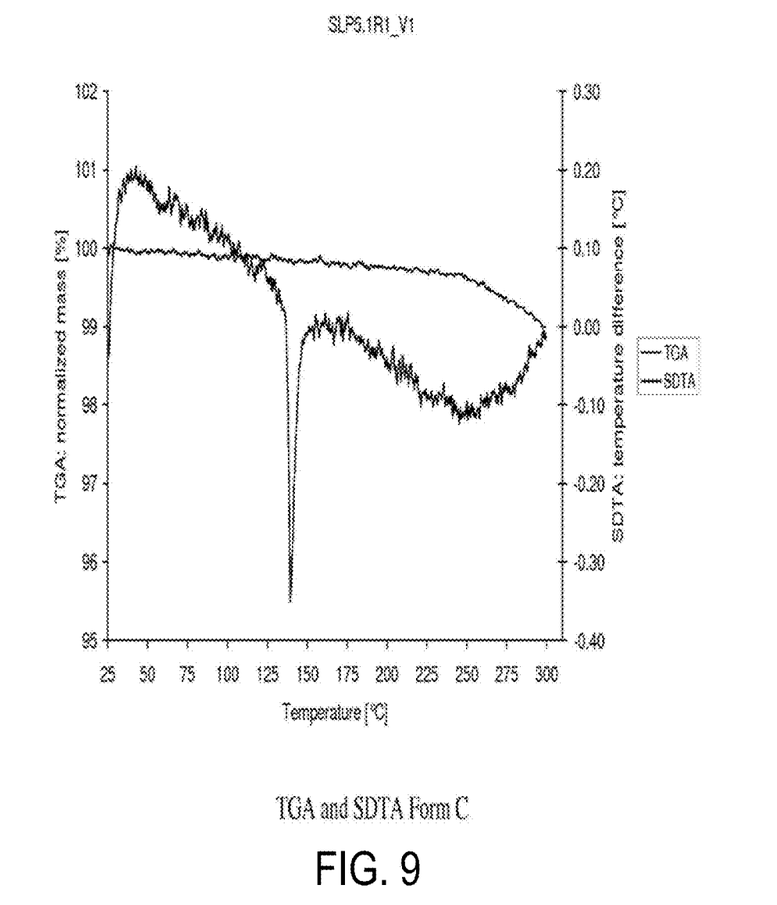
FIG. 9 shows an exemplary TGA and SDTA spectra corresponding to ONA polymorphic form C.
Figure 10:
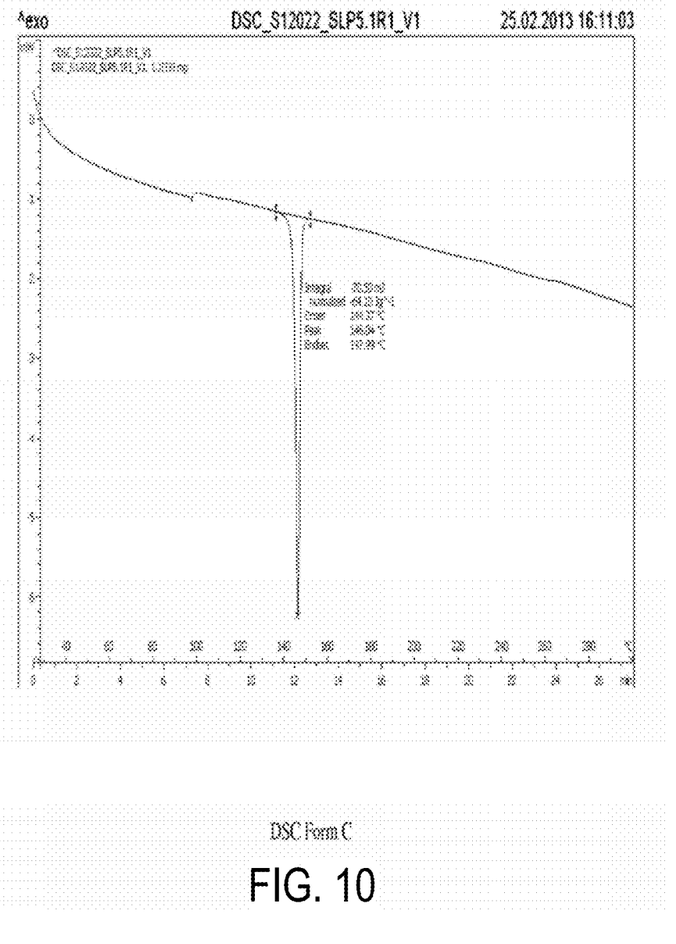
FIG. 10 shows an exemplary DSC corresponding to ONA polymorphic form C.

In one aspect, ONA polymorphic form B has the XRPD pattern as shown in FIG. 8.

Figure 11:
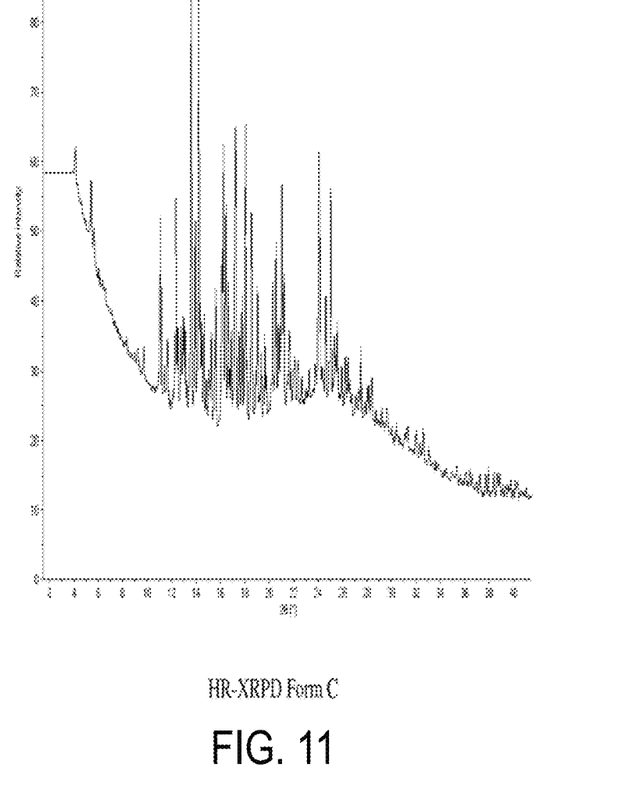
FIG. 11 shows an exemplary HR-XRPD pattern corresponding to ONA polymorphic form C.

In one aspect, ONA polymorphic form C has the HR-XRPD pattern as shown in FIG. 11.

Figure 12:
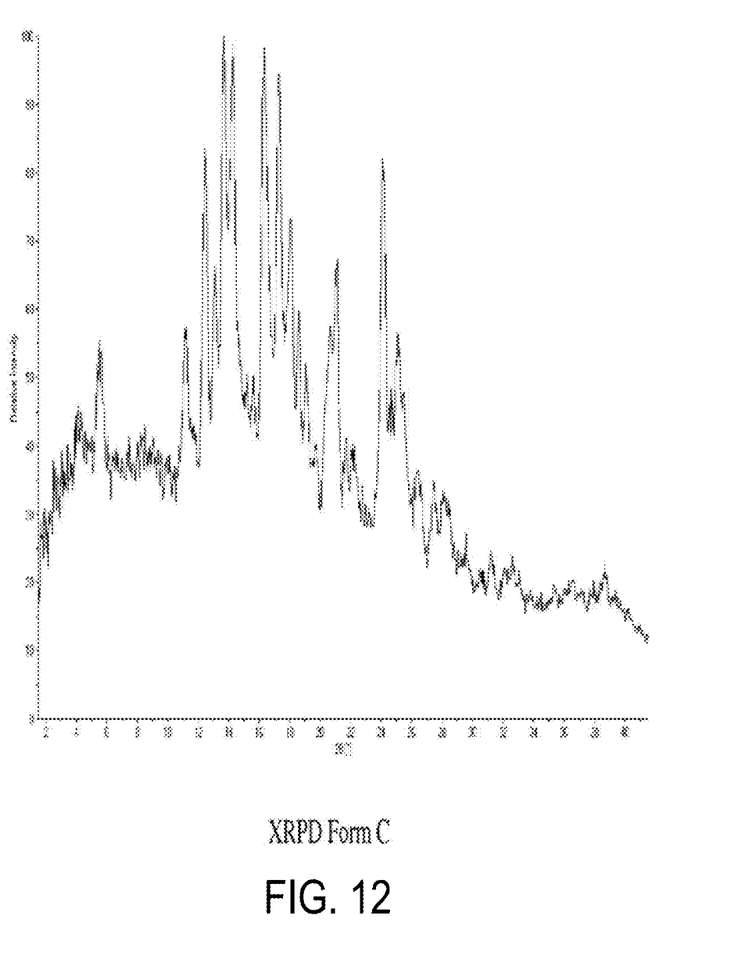
FIG. 12 shows an exemplary XRPD pattern corresponding to ONA polymorphic form C.

In one aspect, ONA polymorphic form C has the XRPD pattern as shown in FIG. 12.

Figure 13:
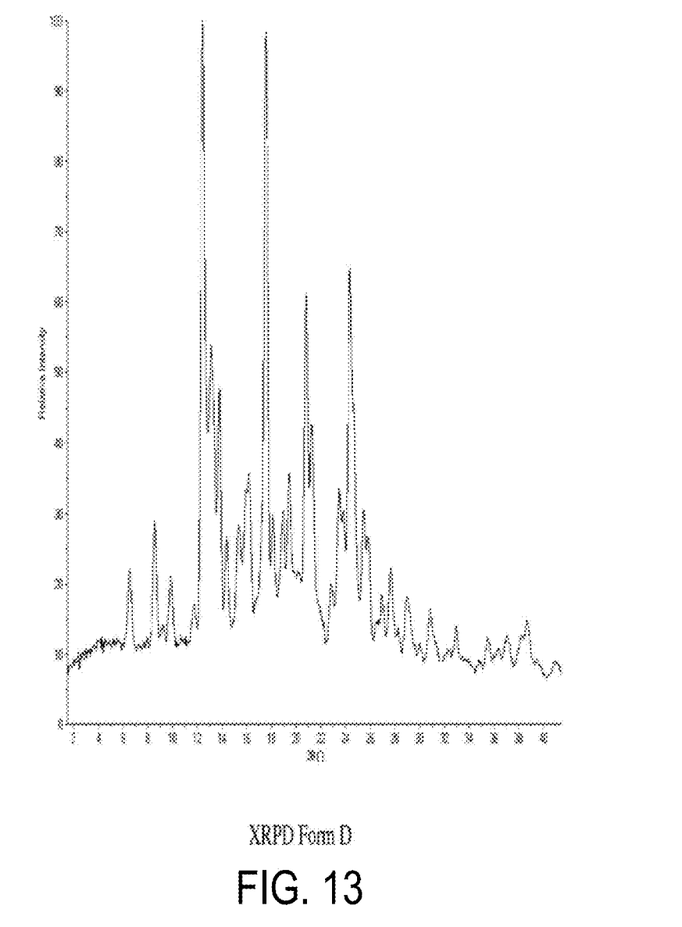
FIG. 13 shows an exemplary XRPD pattern corresponding to ONA polymorphic form D.

In one aspect, ONA polymorphic form D has the XRPD pattern as shown in FIG. 13.

Figure 14:
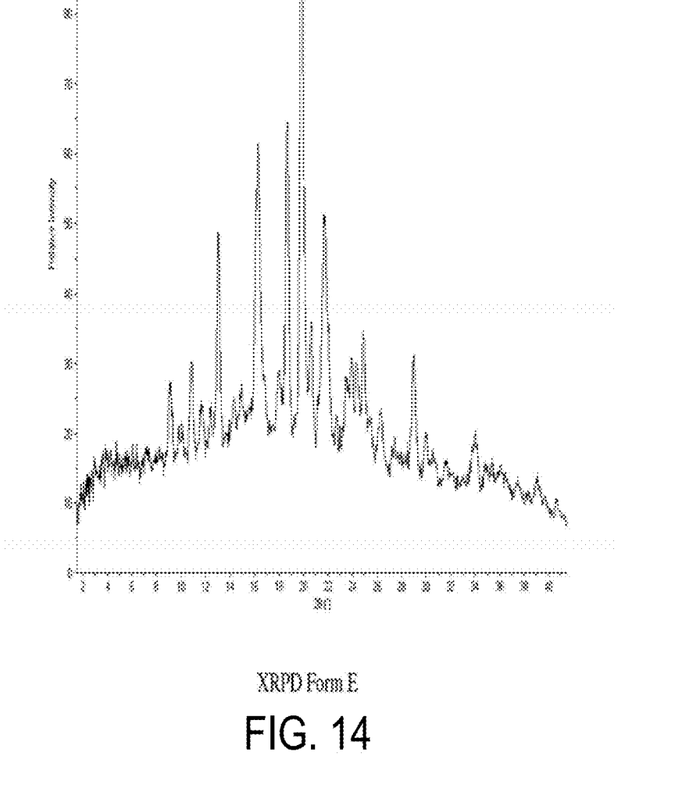
FIG. 14 shows an exemplary XRPD pattern corresponding to ONA polymorphic form E.

In one aspect, ONA polymorphic form E has the XRPD pattern as shown in FIG. 14.

In another aspect, solubility assessment experiments were carried out in a variety of solvents and under the conditions described in Table 2 above.

The ONA polymorphic or crystalline forms can be used to treat a patient in need of treatment as described herein. The terms "treat," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial. The terms "treatment" or "prevention" also refer to delaying onset of a disease for a period of time or delaying onset indefinitely. The term "treatment" or "treating" refers to administering a drug or treatment to a patient or prescribing a drug to a patient or a third party (e.g., caretaker, family member, or health care professional) administers the drug or treatment.

The ONA polymorphic or crystalline forms also encompass derviates. In one embodiment, the term "derivative" includes, but is not limited to, either derivatives, acid derivatives, amide derivatives, ester derivatives and the like. Methods of preparing these derivatives are known to a person skilled in the art. For example, ether derivatives are prepared by the coupling of the corresponding alcohols. Amide and ester derivatives are prepared from the corresponding carboxylic acid by a reaction with amines and alcohols, respectively.

The ONA polymorphic or crystalline forms also encompass hydrates or solvates of ONA polymorphic or crystalline forms (e.g., hemihydrate, monohydrate, dihydrate, trihydrate and the like). Hydrates or solvates of ONA may be prepared by contacting ONA with water or a solvent under suitable conditions to produce the hydrate or solvate of choice.

The ONA polymorphic or crystalline forms also encompass metabolites of ONA polymorphic or crystalline forms. "Metabolite" or "metabolites" refer to any substance produced from another substance by metabolism or a through a metabolic process of a living cell or organ.

Any of the polymorphic ONA forms described herein can be administered or used as starting materials to be administered orally, parenterally (IV, IM, depot-1M, SQ, and depot-SQ), sublingually, intranasally (inhalation), intrathecally, topically, or rectally. Dosage forms known to those of skill in the art are suitable for delivery of the ONA polymorphic forms described herein.

The ONA polymorphic compounds can be formulated into suitable pharmaceutical preparations such as tablets, capsules, or elixirs for oral administration or in sterile solutions or suspensions for parenteral administration. The ONA polymorphic compounds described herein can be formulated into pharmaceutical compositions using techniques and procedures well known in the art.

In one aspect, about 10 to about 200 mg of the ONA polymorphic compounds, or a physiologically acceptable salt, pro-drug, or co-crystal thereof can be compounded or used as a starting material for compounding with a physiologically acceptable vehicle, carrier, excipient, binder, preservative, stabilizer, flavor, etc., in a unit dosage form as called for by accepted pharmaceutical practice. The amount of active substance in compositions or preparations comprising the ONA polymorphic compounds is such that a suitable dosage in the range indicated is obtained.

In another aspect, the compositions can be formulated in a unit dosage form, each dosage containing from about 1 mg to about 1.2 g, or about 2.5 to about 200 mg of the active ingredient. The term "unit dosage from" refers to physically discrete units suitable as unitary dosages for human subjects and other mammals, each unit containing a predetermined quantity of active material calculated to produce the desired therapeutic effect, in association with one or more suitable pharmaceutical excipients.

In one aspect, one or more of the ONA polymorphic compounds are mixed with or used as starting materials mixed with a suitable pharmaceutically acceptable carrier to form compositions. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of the ONA polymorphic compounds described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if the ONA polymorphic compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, the ONA polymorphic compounds described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, the ONA polymorphic compounds and compositions described herein can be enclosed in multiple or single dose containers. The enclosed compounds and compositions can be provided in kits, for example, including component parts that can be assembled for use. For example, an ONA polymorphic compound can be used as a starting material for a lyophilized form and a suitable diluent may be provided as a separated component for combination prior to use. A kit may include ONA polymorphic compound and a second therapeutic agent for co-administration. The ONA polymorphic compound and second therapeutic agent may be provided as separate component parts. A kit may include a plurality of containers, each container holding one or more unit dose of the ONA polymorphic compounds described herein. In one aspect, the containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of the ONA polymorphic compound in the pharmaceutical composition will depend on dissolution, absorption, metabolism, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The ONA polymorphic compounds can be used, for example, in combination with an antitumor agent, a hormone, a steroid, or a retinoid. The antitumor agent may be one of numerous chemotherapy agents (e.g., everolimus, trastuzumab, TM1-D, anti-HER2 drugs, bevacizumab, paclitaxel, docetaxel, taxanes, doxorubicin, liposomal doxorubicin, pegylated liposomal doxorubicin, anthracyclines, anthracenediones, carboplatin, cisplatin, 5-FU, gemcitabine and cyclophosphamide).

In one aspect, solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfate; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue targeted liposomes may also be suitable as pharmaceutically acceptable carriers. These may be prepared according to methods known in the art.

In another aspect, the ONA polymorphic compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, hydroxyl propyl methyl cellulose (HPMC), other cellulose derivatives, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The oral dosage forms can be administered to the patient 1, 2, 3, or 4 times daily. The ONA polymorphic compounds described herein can be administered either three or fewer times, or even once or twice daily. Hence, the ONA employed in the methods of the disclosure be administered in oral dosage form. Whatever oral dosage form is used, they can be designed so as to protect the compounds employed in the methods described herein from the acidic environment of the stomach. Enteric coated tablets are well known to those skilled in the art. In addition, capsules filled with small spheres each coated to protect from the acidic stomach, are also well known to those skilled in the art.

The terms "therapeutically effective amount" and "therapeutically effective period of time" are used to denote treatments at dosages and for periods of time effective to reduce neoplastic cell growth. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.01 µM to about 20 µM. For localized administration, much lower concentrations than this can be effective, and much higher concentrations may be tolerated. One of skill in the art will appreciate that such therapeutic effect resulting in a lower effective concentration of the ONA polymorphic compound may vary considerably depending on the tissue, organ, or the particular animal or patient to be treated. It is also understood that while a patient may be started at one dose, that dose may be varied overtime as the patient's condition changes. In one aspect, the ONA polymorphic compounds can be used to inhibit the growth of tumors derived from tissue including, but not limited to, breast, brain, meningiomas, prostate, ovarian, endometrial, uterine leiomyoma, lung, and uterine tissues.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians who are skilled in this art.

Although the above description refers to particular aspects, it is to be understood that these aspects are merely illustrative. It will be apparent to those skilled in the art that various modifications and variations can be made to the polymorphic forms and methods described herein. Thus, it is intended that the present description include modifications and variations that are within the scope of the appended claims and their equivalents.

What is claimed is:

1. An onapristone crystalline Form A that exhibits an x-ray powder diffraction pattern (XRPD) having characteristic peaks expressed in degrees 2-theta at approximately 21.22, 12.82, 14.34, 16.14, 18.58, 18.18, 16.78, 11.66, 24.02, and 9.74 with a peak tolerance of +/− 0.2 degrees 2-theta.

2. A pharmaceutical composition comprising the onapristone crystalline Form A of claim 1 and a pharmaceutically acceptable excipient, diluent, or carrier.

3. The pharmaceutical composition of claim 2, in a unit dosage form.

4. The pharmaceutical composition of claim 3, wherein the unit dosage form is selected from the group consisting of tablets, pills, capsules, and troches.

5. The pharmaceutical composition of claim 2, where the onapristone crystalline form is present in an amount from about 10 to about 200 mg.

6. The pharmaceutical composition of claim 2, further comprising at least one additional active pharmaceutical agent.

7. The pharmaceutical composition of claim 6, wherein the additional active pharmaceutical agent is selected from the group consisting of an antitumor agent, a hormone, a steroid, or a retinoid.

8. The pharmaceutical composition of claim 7, wherein the additional active ingredient is selected from the group consisting of everolimus, trastuzumab, TM1-D, anti-HER2 drugs, bevacizumab, paclitaxel, docetaxel, taxanes, doxorubicin, liposomal doxorubicin, pegylated liposomal doxorubicin, anthracyclines, anthracenediones, carboplatin, cisplatin, 5-FU, gemcitabine and cyclophosphamide.

* * * * *